US008163317B2

(12) United States Patent
Søe et al.

(10) Patent No.: US 8,163,317 B2
(45) Date of Patent: Apr. 24, 2012

(54) METHOD

(75) Inventors: Jørn Borch Søe, Tilst (DK); Lars Wexøe Petersen, Muskego, WI (US); Charlotte Horsmans Poulsen, Brabrand (DK); Thomas Rand, Copenhagen S (DK); Dana L. Boll, Olathe, KS (US)

(73) Assignee: Danisco A/S, Copenhagen (DK)

( * ) Notice: Subject to any disclaimer, the term of this patent is extended or adjusted under 35 U.S.C. 154(b) by 905 days.

(21) Appl. No.: 11/048,230

(22) Filed: Feb. 1, 2005

(65) Prior Publication Data
US 2005/0202121 A1 Sep. 15, 2005

Related U.S. Application Data

(63) Continuation-in-part of application No. 10/001,136, filed on Nov. 15, 2001, now Pat. No. 6,872,412, and a continuation-in-part of application No. PCT/IB03/05278, filed on Oct. 24, 2003.

(60) Provisional application No. 60/256,902, filed on Dec. 19, 2000, provisional application No. 60/438,852, filed on Jan. 9, 2003.

(30) Foreign Application Priority Data

Nov. 17, 2000 (GB) .................................. 0028119.6
Oct. 30, 2002 (GB) .................................. 0225236.9

(51) Int. Cl.
A23C 9/12 (2006.01)
(52) U.S. Cl. ........................................................ 426/34
(58) Field of Classification Search ...................... 426/34
See application file for complete search history.

(56) References Cited

U.S. PATENT DOCUMENTS

| 4,959,212 | A | 9/1990 | Stancesco et al. |
| 5,010,007 | A | 4/1991 | Prieels |
| 5,626,893 | A | 5/1997 | Reddy |
| 6,358,543 | B1 | 3/2002 | Søe et al. |
| 6,872,412 | B2 | 3/2005 | Søe et al. |
| 2002/0004085 | A1 | 1/2002 | Xu |

FOREIGN PATENT DOCUMENTS

| EP | 0492716 A1 | 12/1991 |
| EP | 1020523 A2 | 7/2000 |
| GB | 740379 | 9/1955 |
| GB | 967574 | 8/1964 |
| JP | 48016612 B | 12/1970 |
| JP | 7-327601 | 12/1995 |
| JP | 9-9862 | 1/1997 |
| RU | 2088115 C1 | 10/1995 |
| SU | 926004 | 5/1982 |
| WO | WO 89/11227 | 11/1989 |
| WO | WO 90/04336 | 5/1990 |
| WO | WO 92/22213 | 12/1992 |
| WO | WO 93/19628 | 10/1993 |
| WO | 96/39851 | 12/1996 |
| WO | 96/40935 | 12/1996 |
| WO | WO 96/40935 | * 12/1996 |
| WO | WO 99/31990 | 7/1999 |

OTHER PUBLICATIONS

Matzdorf, B. et al. 1994. Browning of mozzarella cheese during high temperature pizza baking. J. Dariy Science. 77:2850-2853.*
Hansen, O. C. et al. 1997. Hexose oxidase from the red alga Chondrus crispus. J. Biological Chem.272(17):11581-11587.*
Johnson, M. E. et al. 1985. Nonenzymatic browning of Mozzarella cheese. J. Dairy Sci. 68:3143-3147.*
Biekman E.S.A.; "Toepassing Van Enzyme Bij De Verwerking Van Aardappelen Tot Consumptierprodukten"; Voedingsmiddelen Technologie, Noordervliet B.V. Zeist, NL, 1989, 22(20):51-53. English Abstract enclosed.
Cook M.W, et al.; Safety Evaluation of a Hexose Oxidase Expressed in Hansenula Polymorpha:; Food and Chemical Toxicology, 2003, 41(4):523-529.
Jiang, Z. et al., "Reduction of nonenzymatic browning in potato chips and French fries with glucose oxidase," J. Food Process. Preserv., 13(3): 175-86, 1989 (XP002902512).
Shipe, W.F.; "Enzymatic Modification of Milk Flavor"; American Chemical Society; 1976(47); pp. 57-65.
Whitaker J.R. et al. "Handbook of food enzymology." Marcel Dekker Inc., New York, 2002, p. 429-430.
H.-D. Belitz & W. Grosch, "Food Chemistry", Published 1987, Springer-Verlag, pp. 119-120.
Mottram, et al.; "Acrylamide is formed in the maillard reaction." Nature, 2002, 419:448.-449.
Stadler, et al.; "Acrylamide From Maillard Reaction Products"; Nature Publishing Group (2002); pp. 449.
Gorbatova K.K., "Biochemistry of milk and milk products" (Moscow, KOLOS, 1997 pp. 38-41).
Don Scott, "Glucose Conversion in Preparation of Albumen Solids by Glucose Oxidase-Catalase System", Agricultural and Food Chemistry, Aug. 19, 1953, vol. 1, No. 11, pp. 727-730.
L.A. Underkofler, "Glucose Oxidase: Production, Properties, Present and Potential Applications", Soc. Chem. Ind., London, 1961, pp. 72-86.
Lignin, Pectin and Chitin, "Biomass", Methods in Enzymology, 1988, vol. 161, pp. 306-316.
J.P. Borel et al., "Two dimensional paper chromatography for the detection of oxidation of maltose by glucose oxidase", J. Chromatog., 1971, vol. 55, pp. 425-428.
N. Low et al., "Reduction of Glucose Content in Potatoes with Glucose Oxidase", Journal of Food Science, 1989, vol. 54, No. 1, pp. 118-121.
Charlotte Poulsen et al., "Purification and Characterization of a Hexose Oxidase with Excellent Strengthening Effects in Bread", Cereal Chem., 1998, vol. 75, No. 1, pp. 51-57.

(Continued)

Primary Examiner — D. Lawrence Tarazano
Assistant Examiner — Hamid R Badr
(74) Attorney, Agent, or Firm — Vedder Price P.C.; Thomas J. Kowalski; Deborah L. Lu

(57) ABSTRACT

There is provided a process for the prevention and/or reduction of Maillard reaction in a foodstuff containing (i) a protein, a peptide or an amino acid and (ii) a reducing sugar, the process comprising contacting the foodstuff with an enzyme capable of oxidising a reducing group of the sugar.

10 Claims, 17 Drawing Sheets

OTHER PUBLICATIONS

A.G. Rand Jr., "Direct Enzymatic Conversion of Lactose to Acid: Glucose Oxidase and Hexose Oxidase", Animal Science and Food & Resource Chemistry Departments, University of Rhode Island, 1972, vol. 37, pp. 51-57.

D.J. Dawson, Fermentation Studies on Thermoduric Starters used in High-Temperature Cheddar Cheese Manufacture, Australian Journal of Dairy Technology, Jul.-Sep. 1958, pp. 139-143.

M.A. Thomas, "Browning Reaction in Cheddar Cheese", Australian Journal of Dairy Technology, Dec. 1969, pp. 185-189.

M.E. Bley et al., "Factors Affecting Nonenzymatic Browning of Process Cheese", J. Dairy Science, 1985, vol. 68, pp. 555-561.

Mark E. Johnson et al., "Nonenzymatic Browning of Mozzarella Cheese", J. Dairy Science, 1985, vol. 68, pp. 3143-3147.

Edgar Spreer, "Compositions and characteristics of Milk", Milk and Dairy Product Technology, Marcel Dekker, Inc., 1998, pp. 22-23.

Garcia, et al., Analysis and Modeling of the Ferulic Acid Oxidation . . . , J. Agric. Food Chem (2004) vol. 52, p. 3946-3953.

F. Giffhorn, Fungal Pyranose Oxidases: Occurance, Properties . . . , Appl. Microbiol. Biotechnol. (2000) vol. 54, p. 727-740.

John H. Pazur, et al., Comparison of the Action of Glucoamylase . . . , Carbohydrate Research (1977) vol. 58, p. 193-202.

Rob Schoevaart, et al., Galactose Dialdehyde As Potential Protein . . . , Carbohydrate Research (2002) vol. 337, p. 899-904.

Alberto Sols, et al., On the Substrate Specificity of Glucose Oxidase, Biochim. Biophys, Acta (1957) vol. 24, p. 206-207.

L.A. Underkofler, Properties and Applications of the Fungal . . . , 1958 reprinted from Proceedings of the Int'l Symposium on Enzyme Chemistry, Tokyo and Koyoto 1957, p. 486-490.

Arjan van Wijk, et al., Enzymatically Oxidized Lactose and Derivatives . . . , Carbohydrate Research (2006) vol. 341. p. 2921-2926.

Edwin C. Webb, Enzyme Nomenclature 1992, Academic Press, Inc., p. 56.

P.F. Fox (ed.), Advanced Dairy Chemistry, Chemistry of the Mallard Reaction, Chapman & Hall (1997) vol. 3, p. 167-169.

Gerald Reed (ed.), Enzymes in Food Processing, Academic Press (1975) p. 222-229.

K. Kulp, Enzymes As Dough Improvers, Advances in Baking Technology, Ed. B.S. Kamel, et al., Blackie Academic & Professional (1993) Chapter 7, p. 152 and 173.

Printout: Chemistry Comes Alive! J. Chem Edu (2001) vol. 5, Glucose Oxidase http://jchemed.chem.wisc.edu/JCESoft/CCA/CCA5/MAIN/2BIOCHEM/BIOCHEM2/GLUOXID/GLUOXID3/MOVIE.HTM.

Appeal No. T1310/10-3309, European Patent No. 1 341 422, in the name of Danisco, Aug. 27, 2010.

Opposition to European Patent No. 1 341 422, Jan. 8, 2010.

Curriculum Vitae—Jorn Borch Soe Jan. 2010.

D26: Experimental data entitled Effect of Different Hexose Oxidase and Other Oxido Reductases in Dough, Jun. 24, 2002.

D27: Experimental data entitled Effect on Dough of HOX and GOX on maltose in Dough, Aug. 4, 2003.

D39: Experimental data Investigation of Glucose Oxidase from Cladosporium Oxyporum.

* cited by examiner

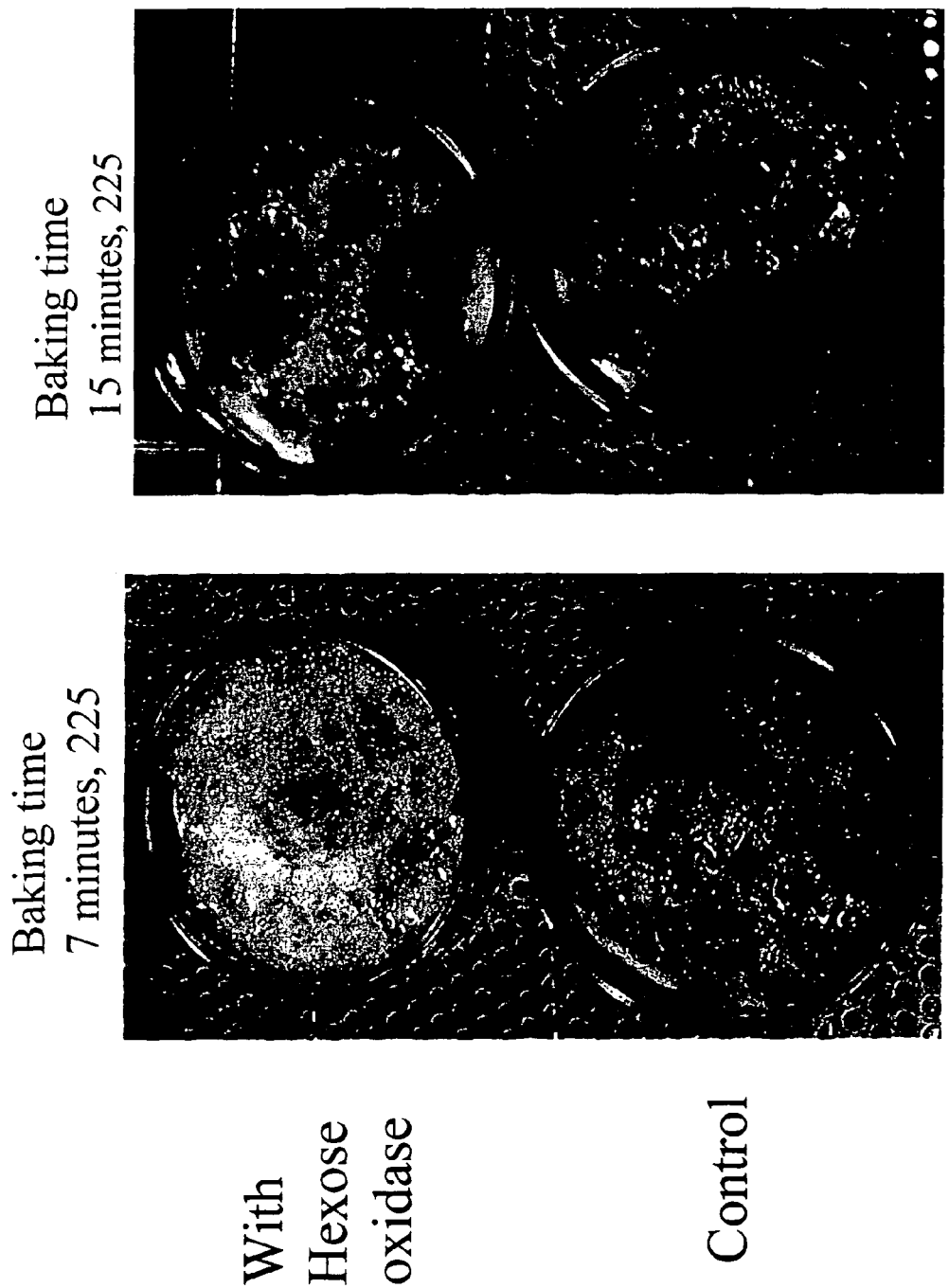

Figure 2 - Mozzarella cheese treated with Hexose

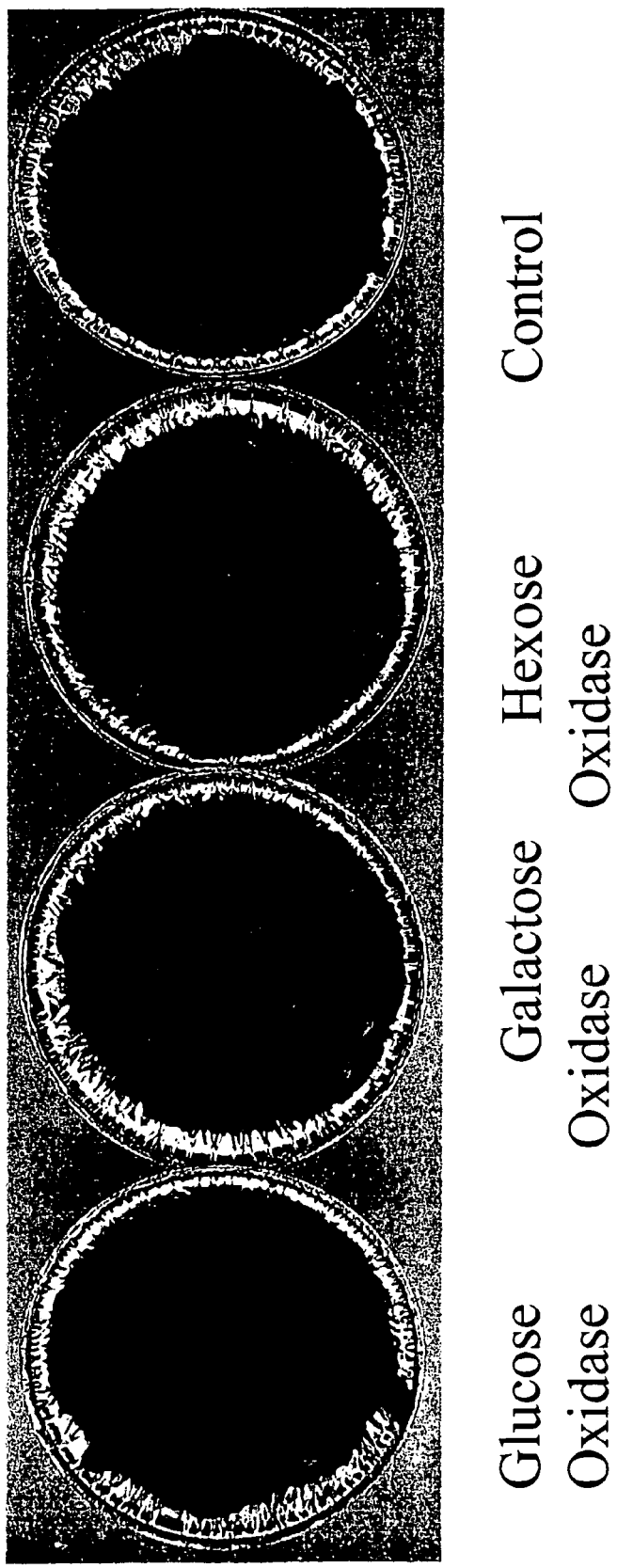
Figure 3 - Mozzarella Cheese treated with oxidative enzymes

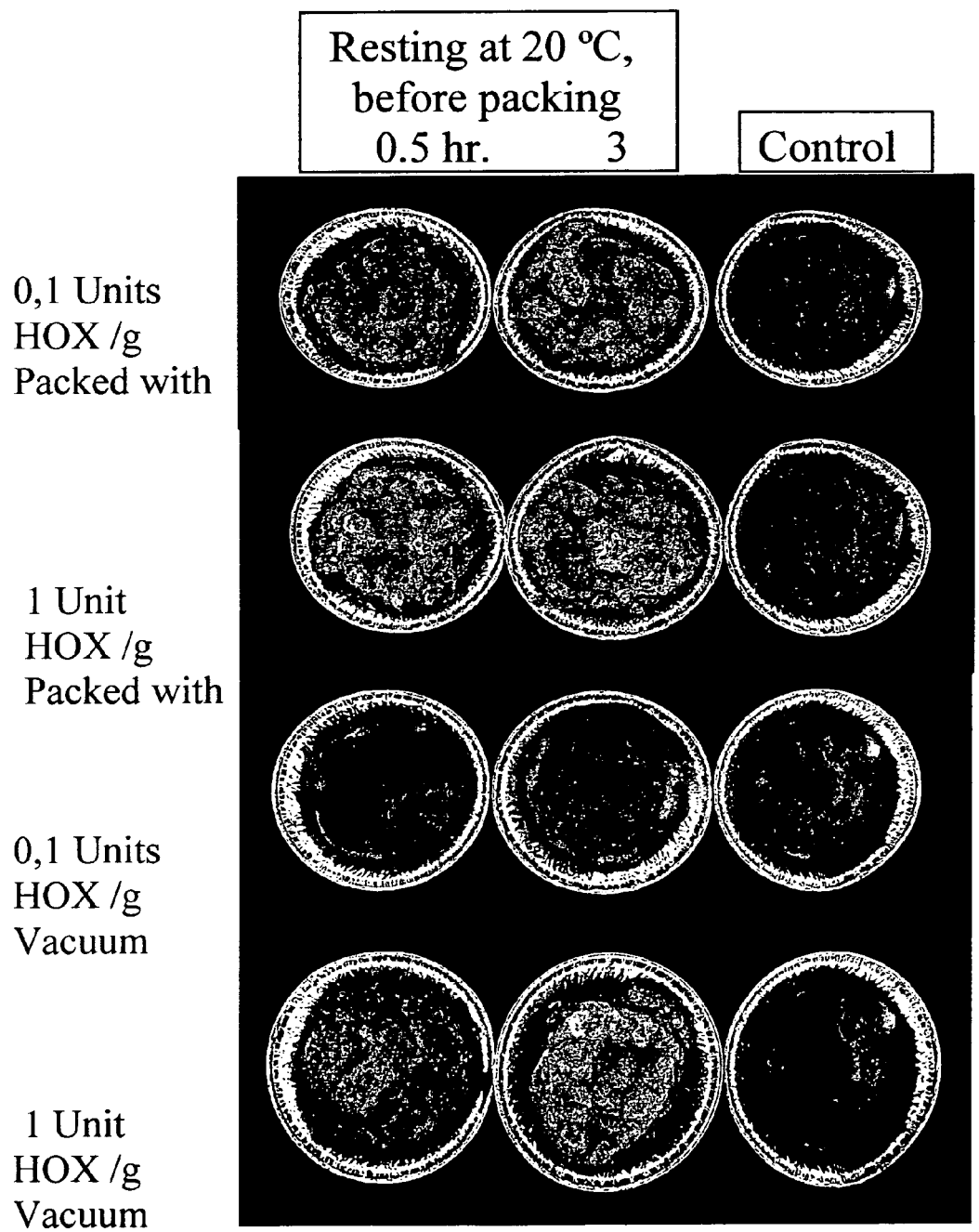
Figure 4 - Mozzarella cheese with Hexose

Figure 5A –
Gratin baked with Hexose Oxidase
Hexose Oxidase        Control

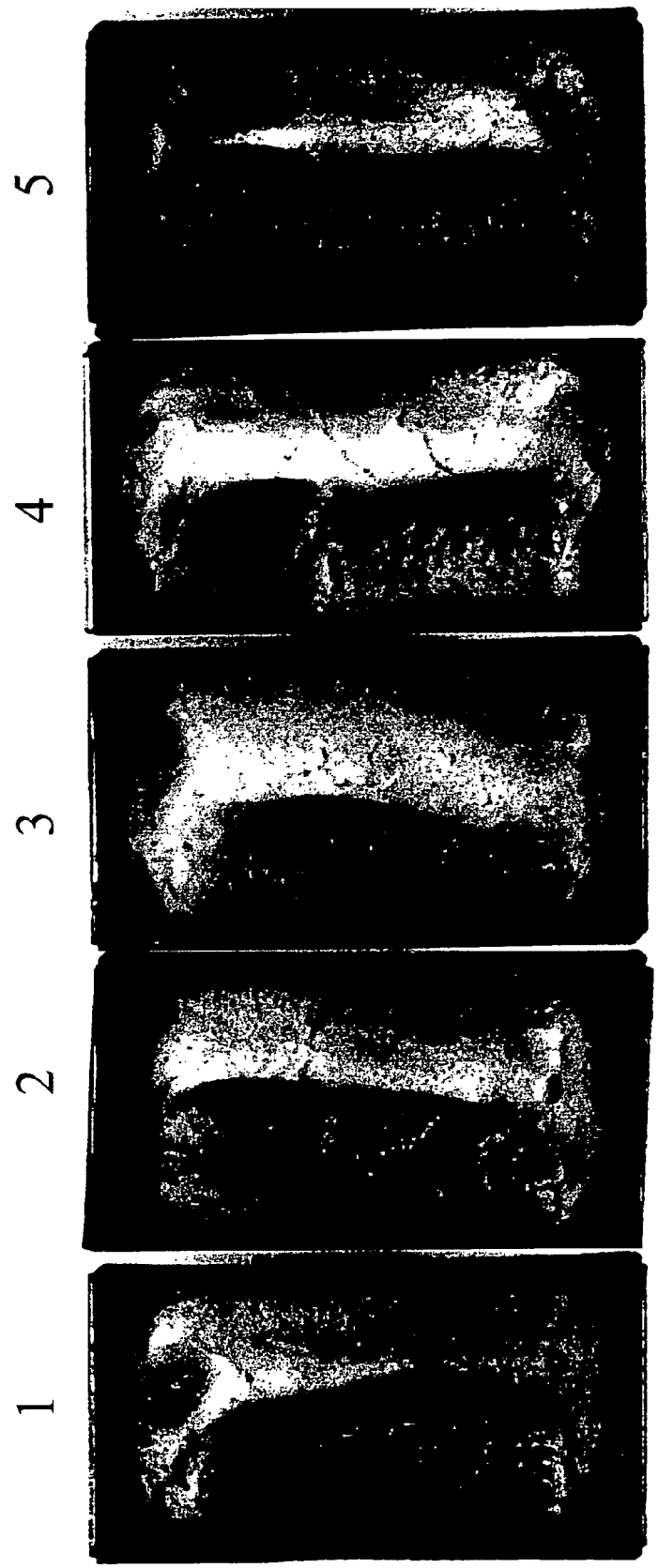
Figure 5B - Gratin baked with Hexose Oxidase

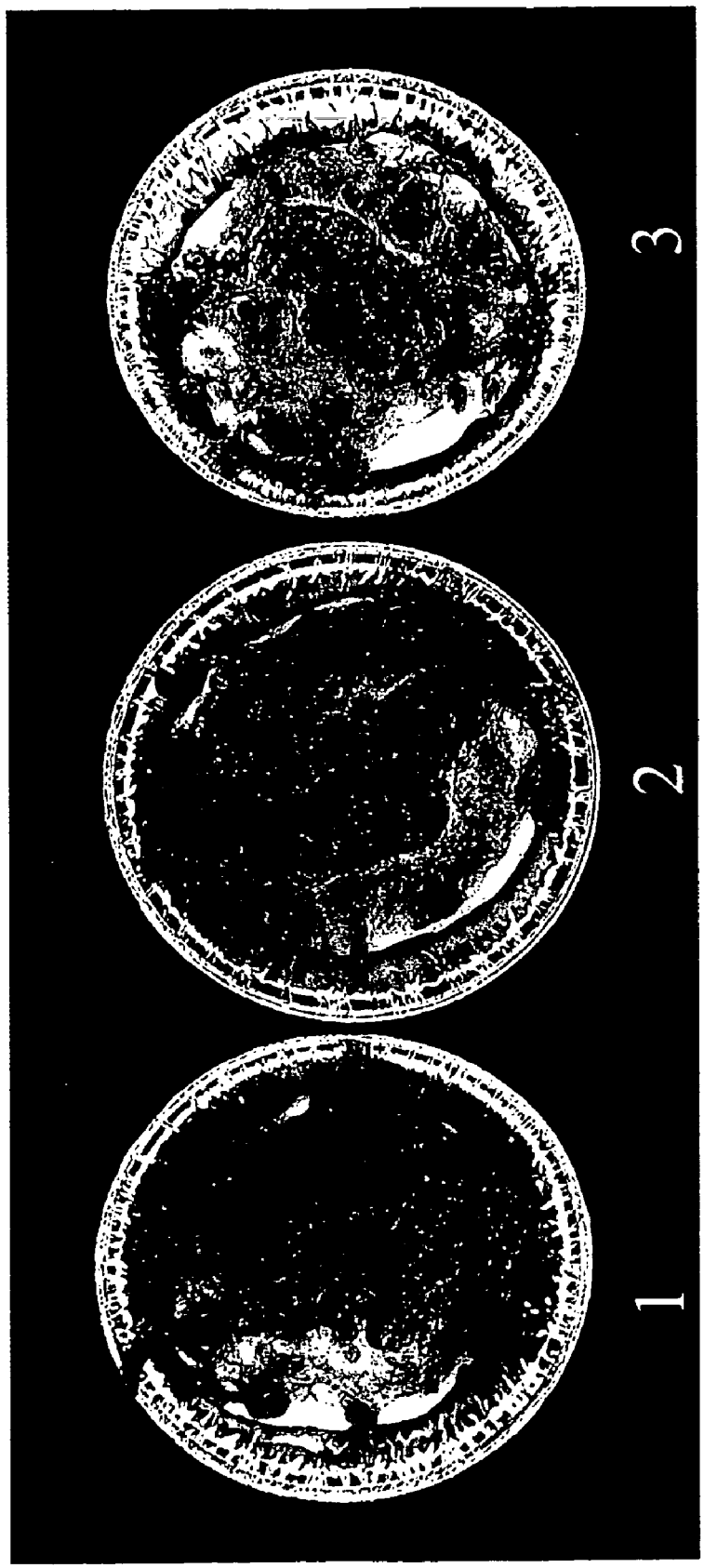
Figure 6 - Low fat Mozzarella cheese treated with Hexose Oxidase

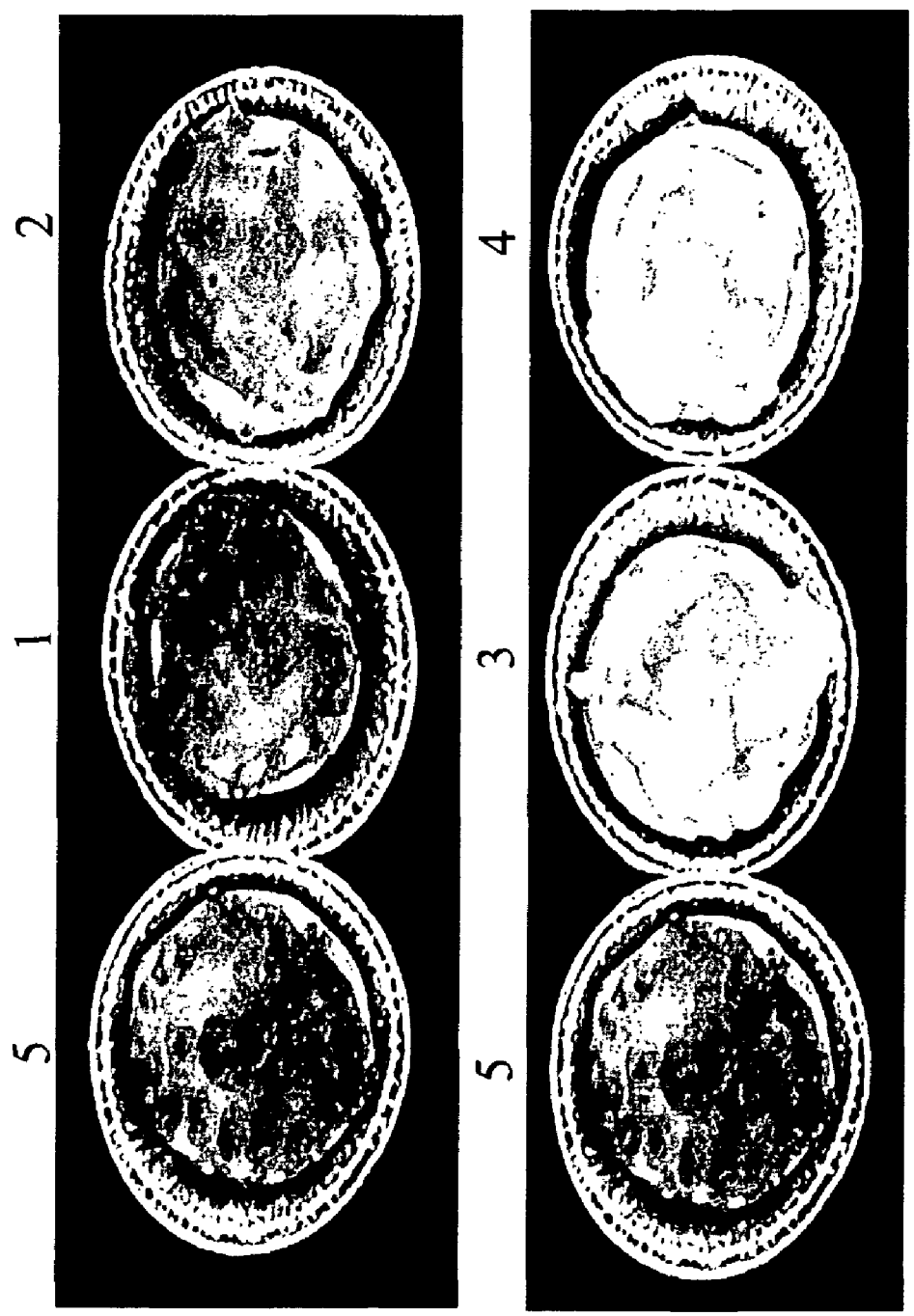
Figure 7 - Mozzarella cheese treated with Hexose Oxidase,

METHOD

RELATED APPLICATIONS

This application is a continuation-in-part of U.S. application Ser. No. 10/001,136 filed Nov. 15, 2001 now U.S. Pat. No. 6,872,412, which claims priority from U.S. Provisional Application 60/256,902 filed Dec. 19, 2000 and United Kingdom Application 0028119.6 filed Nov. 17, 2000. The present application is also a continuation-in-part of International Patent Application No. PCT/IB2003/005278 filed Oct. 24, 2003 and published as WO 2004/039174 on May 13, 2004, which claims priority from United Kingdom Application 0225236.9 filed Oct. 30, 2002 and U.S. Provisional Application No. 60/438,852 filed Jan. 9, 2003. All of the above-mentioned applications, as well as all documents cited herein and documents referenced or cited in documents cited herein, are hereby incorporated herein in their entirety by reference.

FIELD OF THE INVENTION

The present invention relates to the control of Maillard reaction in a foodstuff.

BACKGROUND OF THE INVENTION

Foodstuffs consist of an extremely broad spectrum of constituents. These include nitrogen-containing (proteinaceous) compounds (e.g. one or more free amino acids or their derivatives, protein hydrolysates, intact whole proteins, or a combination of these) plus vitamins, including amino nitrogen containing vitamins, and their derivatives, plus other, non-amino nitrogen-containing compounds, e.g. ammonium compounds such as ammonium sulphate carbohydrates, including
  reducing sugars, e.g. glucose (also known as dextrose), fructose (also known as levulose) and 5-carbon or pentose sugars such as xylose, and other aldehyde containing compounds which may be found, for example in flavouring agents
  non-reducing disaccharide sugars (e.g. sucrose) which may be hydrolysed to produce the reducing sugar moiety, this reaction being promoted by the presence of moisture and elevated temperatures.

Over time, in the presence of moisture, and in even moderate heat (i.e. at temperatures above the freezing point of water), the Maillard reaction occurs.

The Maillard reaction is a reaction consisting of an a nucleophilic attack by a free amino group present in a protein, a peptide or an amino acid on an aldehyde group of a reducing sugar. The reaction products further cause a series of reactions with other proteinaceous amino groups, thereby to form a brown material and to cause a crosslinking between proteins. Historically, Maillard reported in 1912 that a mixed solution of an amino acid and a reducing sugar, when heated, is coloured into brown (L. C. Maillard, Compt. Rend. Soc. Biol., 72, 599 (1912)) and, since then, the reaction is called Maillard reaction. In foodstuffs the Maillard reaction typically comprises the interaction of the nitrogen compounds with the aldehyde groups of reducing sugars or other carbonyl compounds.

In some instances, the browning of a Maillard reaction is desirable, for example with butterscotch confections, caramel, cooked meats, etc. In other instances this reaction is undesirable. For example the Maillard reaction can be problematic in some baked food items such as gratin and cakes in which this browning reaction is not easily controlled. This may result in the attractive brown colour becoming too dark and producing black blisters. Clearly this is not desirable.

Furthermore the Maillard reaction can be problematic in the production of foodstuffs containing a dairy product, in particular cheese, which are cooked at a high temperature. In the area of pizza production there is a pronounced Maillard reaction from the cheese spread on top of the pizza. In the present specification and indeed in the art pasta fileta is referred to as mozzarella.

Many pizza manufacturers bake pizza at temperatures>260° C. At these high temperatures the propensity of the cheese to brown excessively has become a particular concern to the mozzarella industry because the mozzarella manufacturers must deliver cheese that will not make black blisters and brown areas when baked at these high temperatures.

The browning effect from mozzarella cheese is typically caused by residual amount of reducing sugars lactose and galactose left from the cheese production. Therefore many attempts to reduce the browning reactions of mozzarella have been based on attempts to reduce the levels of these sugars, and in particular the level of galactose, in the cheese.

In the traditional manufacture of mozzarella, during normal processing conditions, the fermenting micro-organism ferments only the glucose part of lactose and thus releases galactose into the medium. The cheese is subsequently washed during the manufacturing process, however, typically galactose and lactose remain in the cheese in an amount of 0.3 to 0.5 wt. %. Dr. Norman Olson, Dairy Record, June 1983, p. 112-113 has discussed that the degree of browning of mozzarella is related to the free amino acids and sugar concentration in the cheese, and the browning can be prevented by removing the reactants—usually sugar. He also refers to very strong correlation coefficient between galactose and colour levels of baked cheese. Many attempts to reduce the level of galactose and lactose in mozzarella are mentioned in the literature.

U.S. Pat. No. 3,531,297 discloses a process for manufacturing mozzarella comprising the step of soaking the curd in warm water to extract lactose from the curd, and thereby reduce the final lactose content of the cheese. In general, the lower the lactose content of the final mozzarella, the less tendency there is for the cheese to blister, burn, or char when it is subjected to high temperature baking.

While the process of U.S. Pat. No. 3,531,297 was used extensively on a commercial basis in the United States, and was a desirable commercial process, it does have certain disadvantages. The large curd soaking tanks add to the equipment and plant space costs, and the used soak water, which contains lactose, lactic acid and other substances, can add considerably to the waste disposal burden of an operating plant. Another limitation of the process of U.S. Pat. No. 3,531,297 is that the entire processing operation from the cheese vat to the mixer must be carefully timed, sequenced, and carried out on a substantially continuous basis. In practice, this means that the operators of the plant must almost immediately carry out the mixing of the cheese on the completion of the curd soak.

U.S. Pat. No. 4,085,228 discloses a low-moisture mozzarella prepared using a standard starter culture plus an additional culture selected from *Pediococcus cerevisiae*, *Lactobacillus plantarum*, *Streptococcus faecalis*, *Streptococcus durans*, and *Lactobacillus casei*, or mixtures thereof. Although the cheese is made by the usual processing steps, the cheese product has a reduced lactose sugar (and/or its monosaccharide derivatives) content due to the added culture, which metabolises residual lactose during a cold temperature holding at the end of the process. According to U.S. Pat. No. 4,085,228 the resulting cheese has improved properties for the manufacture of pizza, being substantially non-burning and having improving melt, flavour, and colour characteristics. However, the combination of two or more starter cultures makes the mozzarella cheese production more complicated and moreover, still the cheese will still contain minor amounts of galactose and lactose, which can take part in a Maillard reaction.

Mukherjee, K. K.; Hutkins, R. W. Journal of Dairy Science 1994, 77(10) 2839-2849 have shown that the use of a galactose-fermenting, galactose non-releasing micro-organism as a starter culture can produce of low browning mozzarella cheese. Galactose level below 0.1% in the mozzarella cheese was obtained by using selected micro-organism.

According to M. A. Rudan and D. M. Barbano, 1977 J. Dairy Sci 81:2312-2319 the problem related to too much browning and scorching of mozzarella is more pronounced when using low fat cheese (for example cheese containing 0.25-5.8% fat) rather than using a full fat cheese (for example 21% fat). It is discussed that the problem of over-browning is caused by the cheese surface drying too fast which results in scorching. In Rudan et al. the problem was reduced by spraying a layer of vegetable oil on the mozzarella.

In a review A. H. Jana, Indian Dairyman 44, 3, 1992, p. 129-132 mentions the problems with browning of cheese on baked pizza. It is disclosed that the problem is associated with residues of galactose and lactose in the cheese. A number of measures are disclosed to minimise the problem by controlling the level of galactose. These measures include:

- use of specific combinations of *Streptococcus* and *Lactobacillus* bacteria which are able to ferment galactose. This will reduce the level of galactose in the cheese.
- improved washing of the curd with hot water 60-80° C. during the final heating stage.
- draining of the curd at pH>6.3 resulting in more of the remaining lactose and galactose being fermented.
- moderating the processing temperature in the manufacture of processed mozzarella cheese.
- prompt cooling of mozzarella cheese after moulding, leading to controlled levels of galactose in the cheese.
- reducing the brining period thus avoiding excess salt in the water phase and allowing the lactic starter to ferment more of the residual sugar.
- storing the cheese for a minimum period to reduce the proteolytic formation of free amino groups which are able to react with galactose.

Many of the measures to minimise excessive browning mentioned by A. H. Jana are based on very strict process control or process modifications which are difficult to handle and/or may increase cost or decrease yield.

The addition of enzymes to cheese during the production thereof is known from the art. For example U.S. Pat. No. 5,626,893 teaches the use of glucose oxidase as an oxygen scavenger in anticaking agent for cheese.

The present invention alleviates the problems of the prior art.

Some aspects of the invention are defined in the appended claims.

DETAILED DESCRIPTION OF THE INVENTION

We have found that the problems of excessive browning caused by Maillard reaction of foodstuffs containing a protein and a reducing sugar, in particular baked food products, can be controlled by contacting the foodstuff with an enzyme capable of oxidising the reducing group of the sugar. This is a novel approach in which reducing sugar is oxidised to avoid Maillard reaction by bringing the foodstuff into contact with an enzyme which is capable of performing the necessary oxidation and thereby eliminating the reducing sugar from the foodstuff by conversion.

In the present specification, by the term "prevention and/or reduction of Maillard reaction" it is meant that the extent of a Maillard reaction is reduced and/or the period of time required for completion of a Maillard reaction is increased.

In some aspects preferably the enzyme is capable of oxidising the reducing group of a monosaccharide and the reducing group of a disaccharide.

In some aspects preferably the enzyme is hexose oxidase (EC1.1.3.5) or glucose oxidase (EC1.1.3.4). In a highly preferred aspect the enzyme is hexose oxidase. Preferably the HOX is obtained or prepared in accordance with WO 96/40935.

Hexose oxidase is preferred because glucose oxidase (GOX) has a much higher specificity for glucose and can not eliminate the possible Maillard reaction caused by other sugar like galactose and lactose. Glucose oxidase therefore has limited application for reduction of Maillard reaction in food systems. In dairy products such as cheese, galactose and lactose is mainly responsible for the Maillard reaction.

Hexose oxidase (HOX) is an carbohydrate oxidase originally obtained from the red alga *Chondrus crispus*. As discussed in WO 96/39851 HOX catalyses the reaction between oxygen and carbohydrates such as glucose, galactose, lactose and maltose. Compared with other oxidative enzymes such as glucose oxidase, hexose oxidase not only catalyse the oxidation of monosaccharides but also disaccharides are oxidised. (Biochemica et Biophysica Acta 309 (1973), 11-22).

The reaction of glucose with Hexose Oxidase is

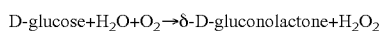

In an aqueous environment the gluconolactone is subsequently hydrolysed to form gluconic acid.

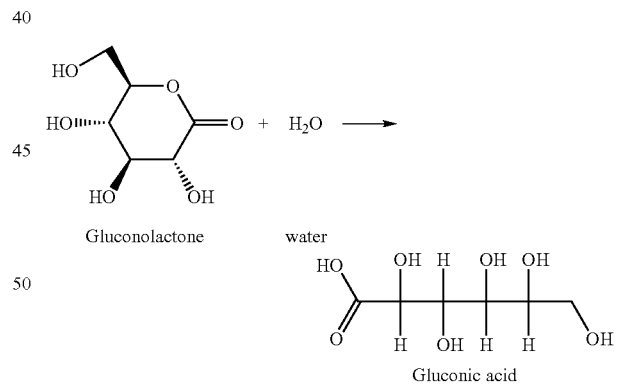

As shown, HOX oxidises the carbohydrate at the reducing end at carbon 1 and thus eliminates the possible Maillard reaction of the carbohydrate.

In a preferred aspect of the present invention the enzyme is capable of oxidising the sugar of the foodstuff at the 1 position. This aspect is advantageous because it ensures that the reducing sugar is oxidised such that the reducing part of the sugar is no longer available to undergo the Maillard reaction. In contrast, for example, galactose oxidase oxidises galactose at carbon 6 leaving the reducing end unchanged. A Maillard reaction therefore can also take place after a galactose oxidase treatment. During cheese making galactose is often accumulated because the micro-organism used to produce cheese can not digest galactose. It might therefore be speculated that galactose oxidase should be able to eliminate galactose and reduce the tendency to Maillard reaction. However, in this preferred aspect of the present invention this is clearly not the case.

In some aspects preferably the reducing sugar is lactose or galactose.

In some aspects preferably the reducing sugar is galactose.

In some aspects preferably the foodstuff is selected from a dairy foodstuff; milk based or milk containing foodstuff, such as gratin; an egg based foodstuff; an egg containing foodstuff; bakery foodstuffs including toasts, bread, cakes; and shallow or deep fried foodstuff such as spring rolls.

When the foodstuff is a dairy foodstuff it is preferably cheese, more preferably mozzarella cheese.

When the foodstuff is cheese the present invention is particularly advantageous. The enzyme of the present invention such as HOX is able to remove reducing sugars in cheese, for example in shredded cheese. Thus it will no longer be so critical to have residues of lactose left in the cheese. It is therefore possible to reduce the number of washings of the cheese curd during the production of the cheese. By reducing the number of washings, the amount of wastewater is also reduced and the yield of cheese is increased.

In some aspects preferably the foodstuff is a potato or a part of a potato. We have found that in the production of cooked potato products the application of the present enzyme reduces unwanted browning. Typical potato products in which the present invention may be applied are French fries and potato chips (crisps).

The enzyme may be contacted with foodstuff during its preparation or it may be contacted with the foodstuff after the foodstuff has been prepared yet before the food stuff is subjected to conditions which may result in the undesirable Maillard reaction. In the former aspect the enzyme will be incorporated in the foodstuff. In the later aspect the enzyme will be present on the surface of the foodstuff. When present on the surface Maillard reaction is still prevented as it is the surface of a material exposed to drying and atmospheric oxygen which undergoes the predominant Maillard reaction.

When contacted with foodstuff during its preparation the enzyme may be contacted at any suitable stage during its production. In the aspect that the foodstuff is a dairy product it may be contacted with the milk during acidification of the milk and precipitation of the milk curd. In this process the enzyme (such as HOX) is not active during the anaerobic conditions created during the acidification and milk protein precipitation, but will be active in the dairy product such as cheese when aerobic conditions are created. Once in aerobic conditions the enzyme oxidise the reducing sugar and reduce the tendency to Maillard reaction.

For application of the enzyme to the surface of the foodstuff, one may apply the enzyme in any suitable manner.

Typically the enzyme is provided in a solution or dispersion and sprayed on the foodstuff. The solution/dispersion may comprise the enzyme in an amount of 1-50 units enzyme/ml, such as 1-50 units Hexose Oxidase/ml.

The enzyme may also be added in dry or powder form. When in wet or dry form the enzyme may be combined with other components for contact with the foodstuff. For example when the enzyme is in dry form it may be combined with an anticaking agent.

In some aspects the present invention further comprises the step of contacting the foodstuff with a catalase.

In a preferred aspect the foodstuff is packaged within an oxygen impermeable container after contact with the enzyme. We have identified that the enzyme on action with the reducing sugar consumes oxygen within a container. Consumption of the oxygen will reduce the microbiological activity in the foodstuff and improve the shelf life. The normal practice of packaging in controlled atmosphere may then be dispensed with.

When the foodstuff is packaged within an oxygen impermeable container after contact with the enzyme it is important that the foodstuff either be allowed to stand before packaging or be packaged with an amount of oxygen within the container. The ant-Maillard reaction which occurs in the present process involves the oxidation of the reducing group of a sugar. For this reaction to occur oxygen is required. If the foodstuff is packaged without standing or without an amount of oxygen within the container, this anti-Maillard reaction may not proceed and the beneficial effects of the present invention may be reduced.

We have also found that the enzyme of the present invention such as HOX may be sufficiently active at low temperatures such that the foodstuff may be refrigerated or frozen after contact with the enzyme without the need to allow the enzyme/reducing sugar reaction to proceed at room temperatures. This is clearly advantageous for the production of foodstuffs where maintenance at elevated temperature may result in unacceptable growth of micro-organisms. Thus in a preferred aspect the process comprises cooling the foodstuff to a temperature of no greater than 5° C. when the majority of the reducing sugar present in the foodstuff contacted with the enzyme has not been oxidised by the enzyme.

It will be appreciated by one skilled in the art that in the practice of the present invention one contacts the foodstuff with a sufficient amount of enzyme to prevent and/or reduce a Maillard reaction. Typical amounts of enzyme which may be contacted with the foodstuff are from 0.05 to 5 U/g (units of enzyme per gram of foodstuff), from 0.05 to 3 U/g, from 0.05 to 2 U/g, from 0.1 to 2 U/g, from 0.1 to 1.5 U/g, and from 0.5 to 1.5 U/g.

The present invention will now be described in further detail by way of example.

BRIEF DESCRIPTION OF THE DRAWINGS

FIG. 1 shows photographs;
FIG. 2 shows photographs;
FIG. 3 shows photographs;
FIG. 4 shows photographs;
FIG. 5A shows photographs;
FIG. 5B shows photographs;
FIG. 6 shows photographs;
FIG. 7 shows photographs.

EXAMPLES

Image Analyses

Figure 8:
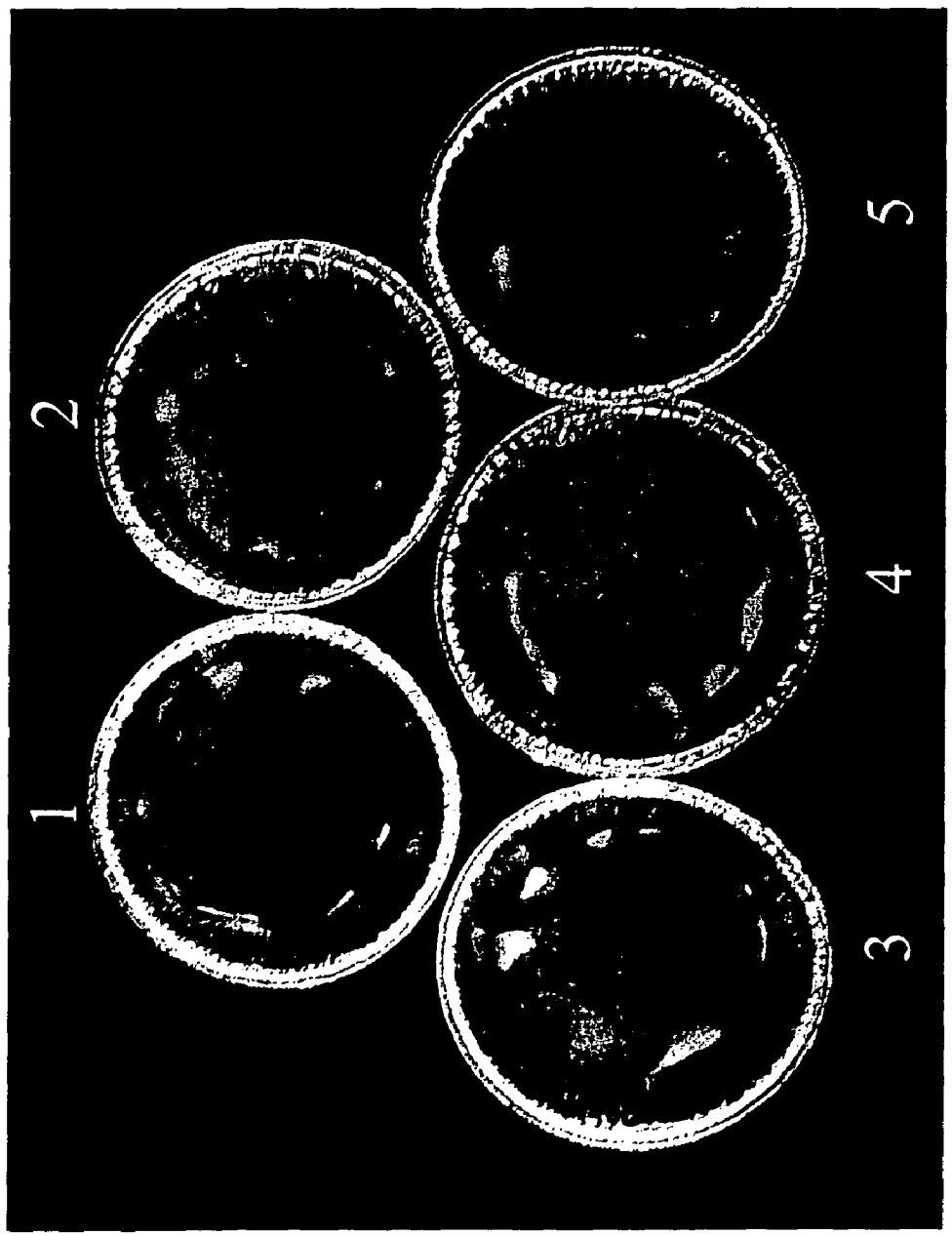
FIG. 8 shows photographs.

Image analysis of the samples of the Examples was performed as follows.

Images of samples are recorded in calibrated non-scattering light intensity by a three chip CCD colour RGB video camera with a resolution of 440000 pixels (JVC KY-F58E). Calibration is done with Kodak's Gray Scale. Through computer based image analysis (Adobe Photoshop including Plug Ins) the images are prepared for quantitative colour measurement of the sample expressed as mean colour intensity of the whole sample, the mean colour intensity of the browned part of the sample and furthermore the relative area of the browned part is calculated. During browning of the sample the green colour intensity decreases significantly and browned areas are then defined as areas with green colour intensity less than 100. The total colour intensity range is from 0-255 (8 bit resolution), where 0 is no intensity and 255 is full intensity. The calibrated light intensity secures that measurements in different series are comparable.

The colour intensity for each pixel is calculated as the average value of the intensities for the red, green and blue colour.

The mean colour intensity is then calculated as the average colour intensity of all the pixels in the sample and in the browned part of the sample respectively. The relative browned area is calculated as the ratio between the number of pixels in the browned part of the sample and the total number of pixels in the whole sample.

Examples 1

Pizza with Mozzarella Cheese 20 g mozzarella cheese (Karoline's Dansk mozzarella, 25% protein, 1% carbohydrate and 21% fat) was scaled in a beaker. 1 ml Hexose Oxidase solution (7.5 HOX units/ml) was sprayed onto the cheese. As a control 1 ml water was sprayed onto another sample of mozzarella cheese. The cheese was stored for 2 hours at room temperature. A dough was made from flour, salt and water. 10 g dough was scaled and placed in a petri dish. 5 grams of mozzarella cheese was placed on top of the dough and baked at 225° C. for 7 min. Another sample was baked for 15 min. After baking the samples were evaluated subjectively. The samples are shown in FIG. 1.

From this test it was clear that the application of hexose oxidase to the cheese reduced the tendency to brown as a result of reduced Maillard reaction. Moreover, in samples which were browned the present invention provided a more even brown colouring without black scorching.

Example 2

Mozzarella cheese was treated in the manner listed in Table 1 using the procedure described in Example 1.

TABLE 1

| Test no | Cheese, g | Water, g | HOX U/g cheese | Storage time, hr. | Storage temperature, ° C. |
|---|---|---|---|---|---|
| 1 | 30 | 1.3 | 0 | 20 | 20 |
| 2 | 30 | 1.3 | 0.01 | 20 | 20 |
| 3 | 30 | 1.3 | 0.05 | 20 | 20 |
| 4 | 30 | | 0 | 20 | 20 |
| 5 | 30 | 1.3 | 0.01 | 20 | 5 |
| 6 | 30 | 1.3 | 0.05 | 20 | 5 |
| 7 | 30 | 1.3 | 0.3 | 20 | 5 |
| 8 | 30 | 1.3 | 0.3 | 20 | 5 |

After the treatment the cheese samples were placed on a dough and baked for 12 minutes at 225° C. After baking the samples were evaluated subjectively. The samples obtained are shown in FIG. 2.

The results show that 0.05 U HOX per g cheese is clearly sufficient reduce the browning of the cheese stored at 20° C. The results also shows that the browning is reduced even if the cheese treated with HOX is stored at 5° C.

Example 3

Mozzarella cheese was treated in the manners listed in Table 2 using the procedure described in Example 1.

TABLE 2

| Test no. | Cheese, g | Enzyme |
|---|---|---|
| 1 | 20 | Control, 1 ml water |
| 2 | 20 | 1 ml Hexose Oxidase, 0.75 Units/ml |
| 3 | 20 | 1 ml Galactose Oxidase, 63 Units/ml |
| 4 | 20 | 1 ml Glucose oxidase 260 Units/ml |

After 20 hours storage at 20° C. the cheese samples were applied onto a dough and baked at 225° C. for 7 minutes. The baked mozzarella samples were evaluated subjectively. The samples obtained are shown in FIG. 3.

The results clearly illustrate that hexose oxidase is very efficient in reducing the extent of Maillard reaction. Glucose oxidase and galactose oxidase only have limited impact on the extent of Maillard reaction.

Example 4

The following example was performed in order to investigate the effect of applying enzyme, in particular hexose oxidase, at different conditions. We studied whether the manner of application of hexose oxidase onto mozzarella cheese might be a critical parameter for the prevention of Maillard reaction in mozzarella cheese normally stored at 5° C. and packed under controlled conditions.

The tests of Table 3 were performed using mozzarella cheese (Karoline's Dansk mozzarella, 25% protein, 1% carbohydrate and 21% fat).

TABLE 3

| Test no. | Hexose Oxidase Unit/g cheese | Resting time, hr before packing | Packing Condition |
|---|---|---|---|
| 1 | 0.1 | 0.5 | Air |
| 2 | 1 | 0.5 | Air |
| 3 | Control | 1.5 | Air |
| 4 | 0.1 | 3 | Air |
| 5 | 1 | 3 | Air |
| 6 | 0.1 | 0.5 | Vacuum |
| 7 | 1 | 0.5 | Vacuum |
| 8 | Control | 1.5 | Vacuum |
| 9 | 0.1 | 3 | Vacuum |
| 10 | 1 | 3 | Vacuum |

The samples were packed in aluminium bags. Half of the samples were vacuum packed and the other half were packed with normal atmospheric air. All samples were stored at 5° C. After 1 week storage the cheese samples were baked for 12 minutes in the manner described in Example 1. After baking the samples were evaluated. The samples obtained are shown in FIG. 4.

The results clearly illustrate the effect of adding HOX to the cheese. The results further show that reduction in Maillard reaction may be obtained for products packed in air and products packed under a vacuum after a resting period.

Example 5

The effect of hexose oxidase on browning was tested in a gratin made by the following procedure.

75 g shortening (mp. 35° C.) and 100 g flour were heated in a pot during mixing. 350 ml skim milk (preheated to 90° C.) was added during continued mixing. Salt and pepper was added. 4 eggs were divided into yolk and egg white. The egg yolks were added individually. The egg white was whipped to a foam with 10 gram baking powder and mixed carefully into the dough. The dough was placed in 2 aluminium trays. One of the trays was sprayed with a solution of hexose oxidase 7.5 Units/ml and kept at room temperature for 30 minutes. The gratin was then baked in a air circulating oven at 175° C. for 20 minutes. After baking the gratin was evaluated visually. The samples obtained are shown in FIG. 5A. Further sample were treated in the manner of Table 6 below.

TABLE 6

| Sample | Enzyme added | | Mean Brown Colour |
|---|---|---|---|
| 1 | 0.1 ml water | | 117 |
| 2 | 0.1 ml HOX solution | 0.75 U/ml | 109 |
| 3 | 0.1 ml HOX solution | 1.50 U/ml | 111 |
| 4 | 0.1 ml HOX solution | 7.50 U/ml | 134 |
| 5 | Control | | 116 |

After baking the gratin was evaluated visually. The samples obtained are shown in FIG. 5B. The mean brown colour measurements performed by image analysis indicate that HOX solution containing 7.5 U/ml gives less brown colour (higher values indicate less browning). The other values for mean brown colour are not significantly different form the control.

The results show that the application of HOX gives a less dark surface of the gratin indicating that the Maillard reaction is reduced.

Example 6

The effect of HOX on browning of mozzarella was tested in a low fat mozzarella cheese (Cheasy: 13% fat, 33% protein and 1.5% carbohydrates). The cheese samples were given the following treatment
1: Control 1 ml water added to 20 gram cheese
2: 0.2 ml HOX (7.5 Units/ml) to 20 gram cheese.
3: 1 ml HOX (7.5 Units/ml) to 20 gram cheese.

The enzyme was applied onto the cheese by spraying a solution of the enzyme onto the shredded cheese. The samples were stored at 5° C. for 20 hours and then placed onto a dough in an aluminium tray and baked for 10 minutes at 225° C. in an air circulating oven. After baking the samples were evaluated. The samples are shown in FIG. 6.

The results clearly illustrate the ability of HOX to reduce the excessive browning of a low fat mozzarella cheese. It is also clear that the reduction of browning is dependent on the dosage of hexose oxidase.

Example 7

The effect of hexose oxidase on browning of mozzarella was studied by spraying different level of HOX onto mozzarella cheese. After spraying the HOX solution the cheese was stored for 30 minutes or 3 hours at room temperature and then vacuum packed in an aluminium bag. After 14 days storage at 5° C. the cheese samples were placed on top of a pizza dough and baked for 8 minutes at 225° C. After baking the samples were evaluated visually and pictures of the samples were analysed by a image analyser. The samples of this experiment are shown in FIG. 7: The results of the image analysis are given in Table 7

TABLE 7

| Test no. | Hexose Oxidase Unit/g cheese | Resting time, hr before packing | Mean Pizza Colour | Mean Brown colour | % Brown area |
|---|---|---|---|---|---|
| 1 | 0.1 | 0.5 | 125 | 106 | 61 |
| 2 | 0.1 | 3 | 146 | 122 | 22 |
| 3 | 1 | 0.5 | 173 | 125 | 0.9 |
| 4 | 1 | 3 | 172 | 127 | 0.6 |
| 5 | Control | 1.5 | 123 | 107 | 63 |

As shown in FIG. 7 the browning reaction is strongly reduced by addition of hexose oxidase to the mozzarella cheese. It is also clear that the browning is dependent on the dosage of HOX. It is also observed that the resting time before vacuum packing is important. In particular, at a dosage of 0.1 U/g a resting time of 0.5 h before packaging appears not to be sufficient to substantially reduce Maillard browning. However a resting time of 3 h at this dosage is sufficient. At a dosage of 1 U/g a resting time of either 0.5 h or 3 h before packaging significantly reduces Maillard browning. The differences shown in FIG. 7 are confirmed by the mean colour measurement where lower value indicate a more brown product. Also the % of browned area is also strongly influenced by the addition of HOX to the cheese.

Example 8

Assay Method for Determination of Hexose Oxidase Activity (HOX Assay)

Principle. The HOX assay is based on the measurement of hydrogen peroxide generated in the oxidation of glucose. The hydrogen peroxide is oxidised with ABTS in presence of peroxidase to form a dye.

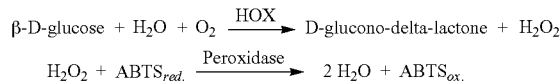

$$\beta\text{-D-glucose} + H_2O + O_2 \xrightarrow{\text{HOX}} \text{D-glucono-delta-lactone} + H_2O_2$$

$$H_2O_2 + ABTS_{red.} \xrightarrow{\text{Peroxidase}} 2\,H_2O + ABTS_{ox.}$$

Reagents
1. 100 mM phosphate buffer, pH 6.3
2. 55 mM D-glucose (SIGMA, G-8270) in 100 mM phosphate buffer, pH 6.3
3. ABTS (SIGMA, A 1888), 5.0 mg/ml in distilled water
4. Peroxidase (SIGMA, P-6782), 0.10 mg/ml in 100 mM phosphate buffer, pH 6.3
Substrate:
4.600 ml reagent 2
0.200 ml reagent 3
0.200 ml reagent 4
Assay
290 µl Substrate and
10 µl enzyme solution The reaction is initiated by the addition of enzyme solution. The mixture is incubated at 25° C. and kinetics of the reaction are measured for 10 minutes on a spectrophotometer (405 nm). The blank sample contains all the components except for the enzyme solution which is replaced by water. From the measurement the slope of OD/min curve is calculated.

Hydrogen Peroxide Standard Curve

A hydrogen peroxide standard curve can be constructed by using varying concentrations of freshly prepared $H_2O_2$ solution (MERCK perhydrol 107298). One unit of enzyme activity is defined as the amount of enzyme which produced 1 µmol of $H_2O_2$ per min at 25° C.

Example 9

The effect of HOX on browning of pizza cheese was tested in combination with catalase. The purpose of adding catalase in combination with HOX is to eliminate hydrogen peroxide formed by the catalytic conversion of lactose and galactose to the corresponding acids, because hydrogen peroxides may engage in some unwanted side reactions and create off flavour by for example lipid oxidation.

Catalase catalyses the following reaction:

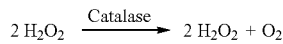

$$2\,H_2O_2 \xrightarrow{\text{Catalase}} 2\,H_2O_2 + O_2$$

In this experiment 60 g Mozzarella cheese (Karolina's Dansk Mozzarella, 25% protein, 1 g carbohydrate and 21% fat) was treated with the amounts of enzyme shown in Table 7

TABLE 7

| Test no. | Units HOX/g cheese | Units Catalase/g cheese |
|---|---|---|
| 1 | 0 | 0 |
| 2 | 0.5 | 0 |
| 3 | 0 | 1 |
| 4 | 0.5 | 1 |
| 5 | 0.17 | 0.33 |

The catalase used is from Sigma cat. No. C3515.

Procedure: Enzyme solutions of HOX and catalase were sprayed onto the mozzarella cheese, and then stored at room temperature for 2 hours. 8 gram of the enzyme treated cheese is then placed on top of 16.7 gram of dough in an aluminium tray and baked at 275° C. for 6 minutes.

The results of the baking experiments are shown in FIG. 8.

From the results in FIG. 8 it is clear that the addition of 0.5 U HOX/g cheese (test 2) reduces the Maillard reaction and gives less browning of the cheese. The same effect is also seen when 0.5 U HOX/g is combined with 1 U Catalase/g (test 4). Catalase alone (test 3) do not contribute to any reduction in Maillard reaction.

Example 10

In the above Examples we have shown that HOX is able to oxidise reducing sugars in Mozzarella cheese and thus reduce the tendency to Maillard reaction when Mozzarella cheese is baked.

In these experiments HOX was applied by spraying a solution of HOX onto the cheese. This may create problems of handling because the cheese becomes wet and sticky this may be limit the application of the shredded cheese to pizza or other food items.

To overcome this problem we applied HOX to Mozzarella cheese in powder form. This is a very convenient way to add the enzyme because an anticaking agent such as starch is normally added to shredded cheese like Mozzarella to avoid stickiness during storage.

In the following experiment HOX was added as a powder to Mozzarella cheese at two concentration 1 U/g and 0.1 U/g cheese and at 25 and 5° C.

Experimental

HOX in powder form is mixed with potato starch. 1.5 g potato starch with HOX is mixed with 98.5 g Mozzarella cheese to give a final dosage of 1 unit or 0.1 unit HOX pr gram cheese. As a control Mozzarella cheese is mixed with potato starch without any HOX.

Example 10a 100 g cheese is placed in a blue cap bottle (310 ml) and an oxygen sensor is placed in the bottle with a sealed cap. Oxygen consumption as a function of time is recorded.

Figure 9:
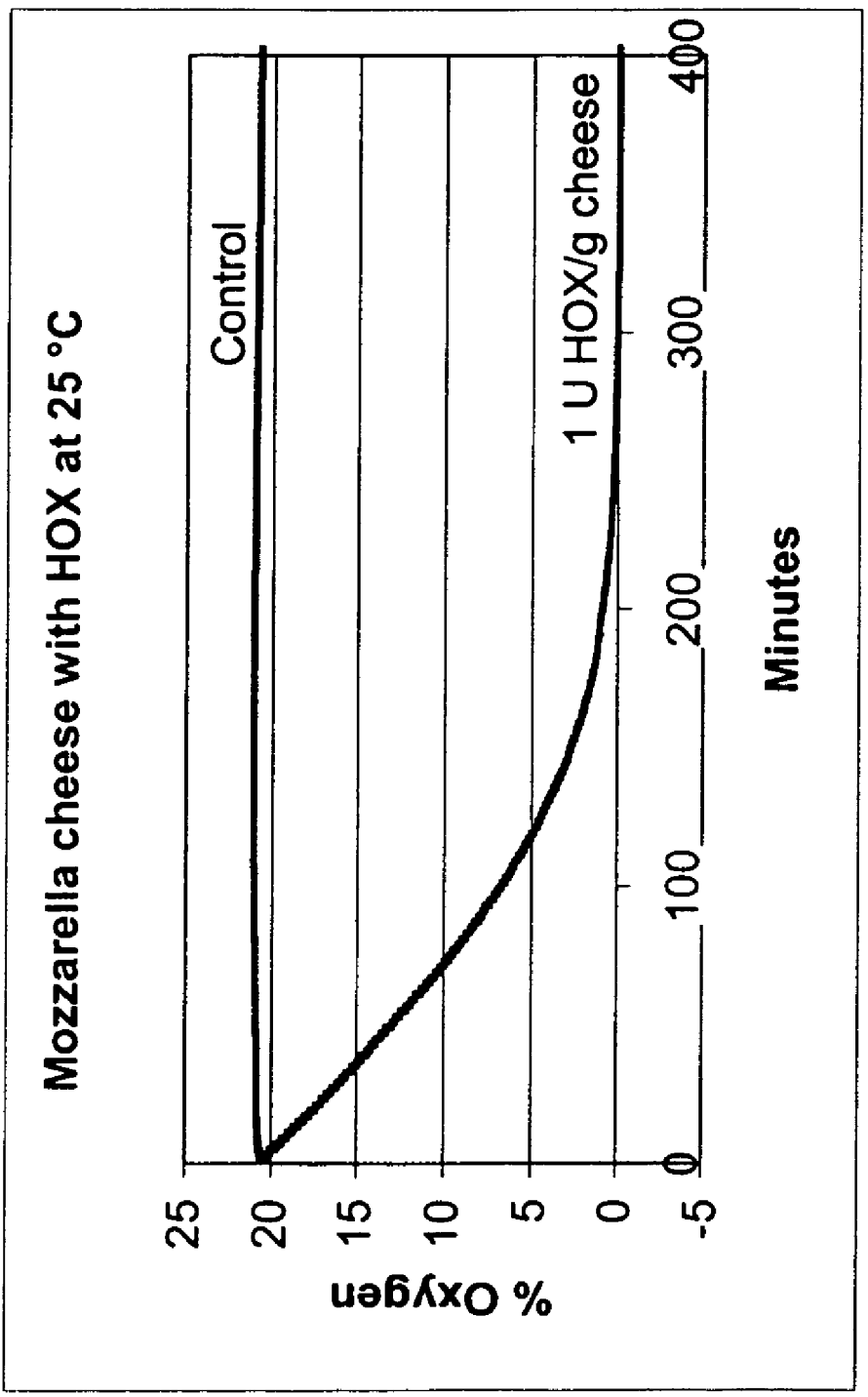
FIG. 9 shows a graph.

1 U HOX/g cheese was tested at 25° C. and the oxygen level in the bottles registered as a function of time FIG. 9. This result clearly illustrate that HOX is also active when it is added as a powder to the cheese. This is surprising as it might be speculated that HOX added as a powder under conditions with lower water activity may be less efficient.

As shown in FIG. 9 all the oxygen in the bottle is consumed by HOX.

Based on the volume of air in the bottle it is calculated that 0.018 mol oxygen is consumed. From the knowledge that HOX oxidises one mol lactose during consumption of one mol oxygen it is calculated that 0.62% lactose is oxidised. From the knowledge about typical level of remaining sugar in Mozzarella cheese it is concluded that almost all the reducing sugar is oxidised. This provides evidence that that diffusion of sugar or HOX occurs with in the cheese.

Example 10b

Figure 10:
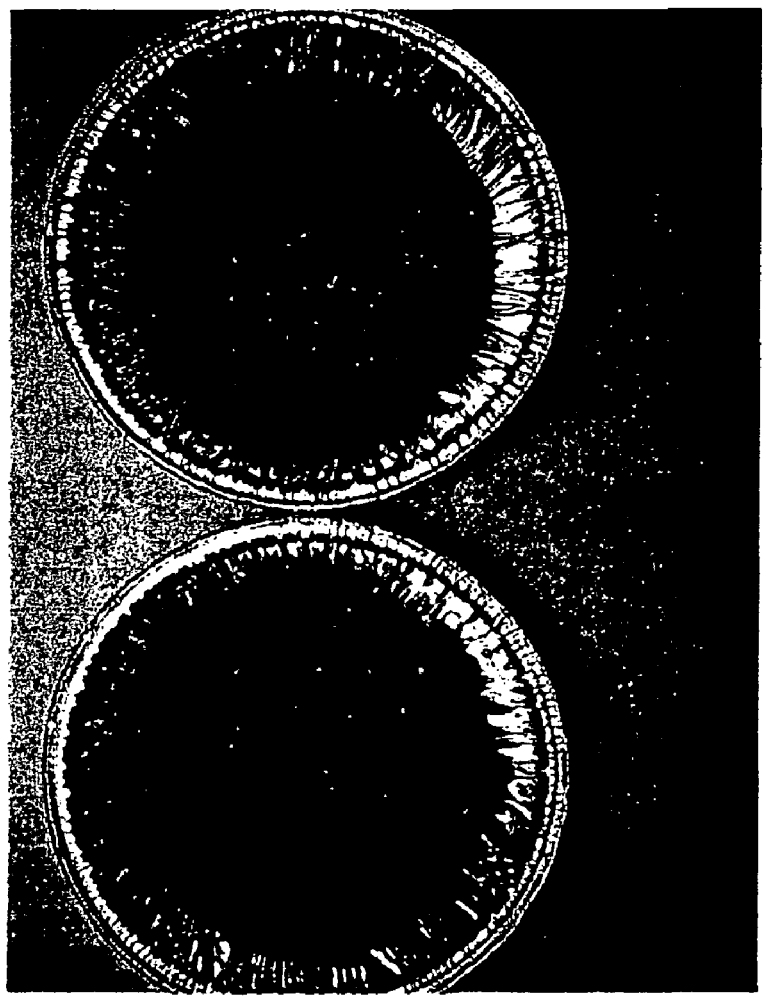
FIG. 10 shows a photograph.

After one day, 10 g cheese is placed in a aluminium tray and baked at 275° C. for 6 minutes. Results from the baking test are shown in FIG. 10. FIG. 10 clearly shows that HOX reduces the browning effect during baking.

Example 10c

Figure 11:
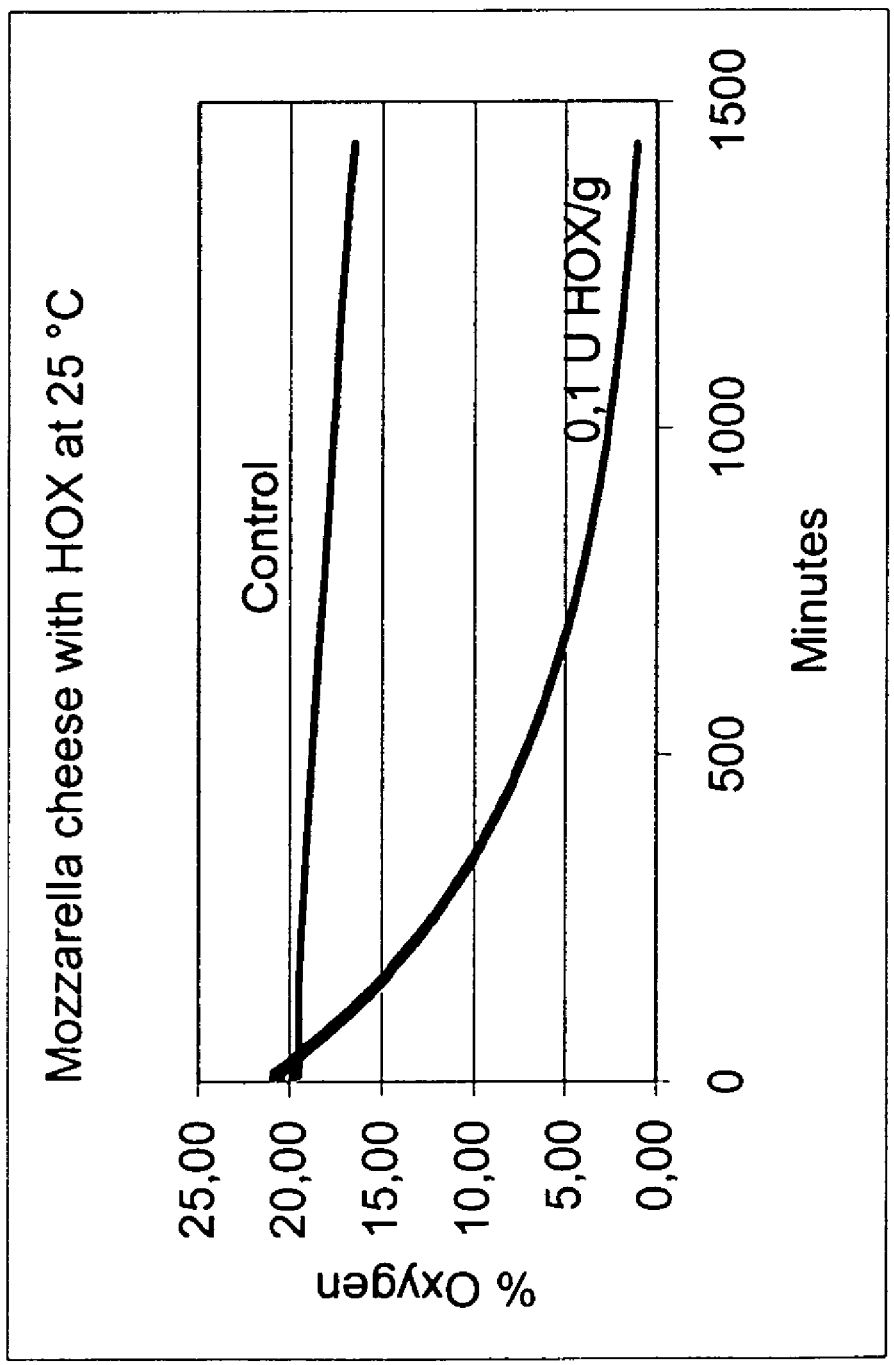
FIG. 11 shows a graph.

In the next experiment only 0.1 U HOX/g cheese was added, and 100 g cheese was stored at 25° C. in a closed bottle (310 ml) with an oxygen sensor. The oxygen consumption was followed as a function of time as shown in FIG. 11.

As expected the reaction was slower because of the lower HOX addition, but also in this experiment it was clear that a main part of the remaining sugar was oxidised within one day.

Example 10d

As cheese is normally stored in a refrigerator after being packed it is of interest to know whether HOX also under these conditions is able to oxidise reducing sugars in cheese.

In this experiment 1 U HOX/g cheese was added to Mozzarella cheese, and 100 g cheese was stored at 5° C. in a closed bottle (310 ml) with an oxygen sensor. The oxygen consumption was followed as a function of time as shown in FIG. 12.

Figure 12:
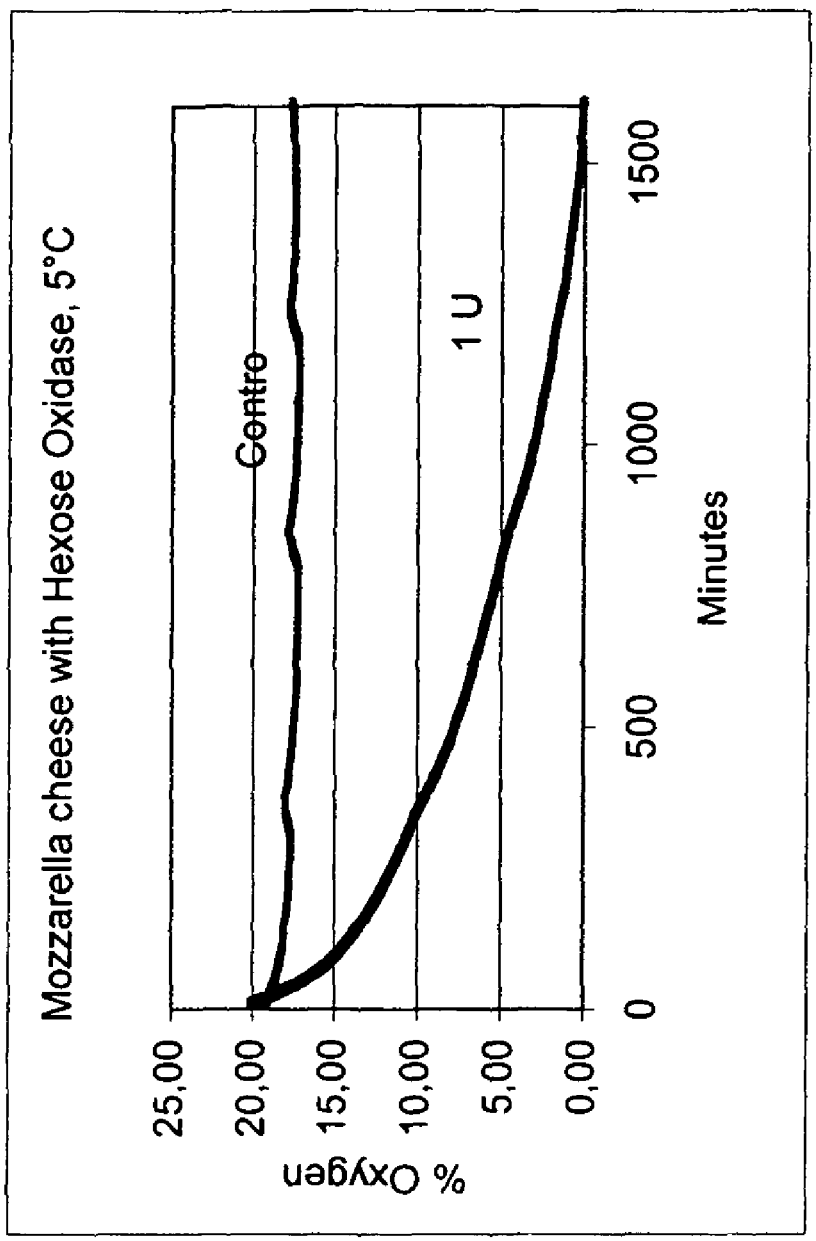
FIG. 12 shows a graph.

The results in FIG. 12 clearly show that HOX is active at 5° C. during consumption of all the oxygen in the bottle. From a production point of view this might be of benefit, because the reaction does not rely on keeping the temperature at room temperature or higher, but the cheese treated with HOX can immediately be stored at 5° C. where reducing sugars are oxidised to the corresponding acid, which will reduce the ability of the cheese to produce Maillard reaction when the cheese is baked. As a further benefit the oxygen in the package is consumed, which will reduce the microbiological activity in the cheese and improve the shelf life, and packaging in controlled atmosphere might be dispensed with.

Based on the oxygen measurements in the bottles with cheese it is possible to calculate the velocity of oxidation expressed as oxygen consumption per minute.

Figure 13:
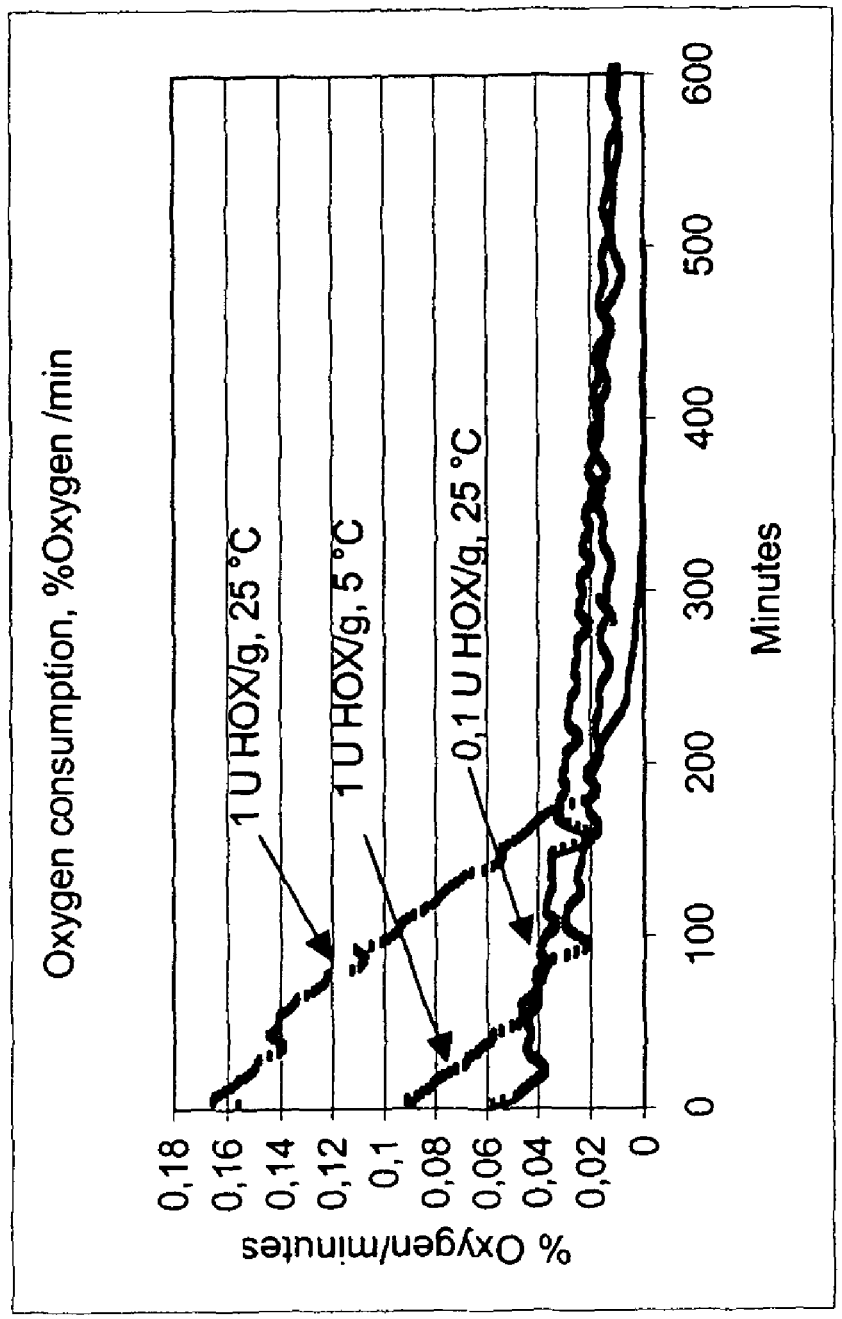
FIG. 13 shows a graph.

In FIG. 13 the oxidation velocity is shown to cheese treated with HOX at different conditions.

The reaction rate at 25° C. is as expected higher than at 5° C. when 1 U HOX/g cheese is added, and it is expected that the diffusion of substrate and enzyme, not the enzyme concentration, which are the limiting factors.

When 0.1 U HOX/g is added the change in oxidation rate is much smaller and this indicate that at this dosage there is a balance between enzyme activity and substrate diffusion in the cheese.

Example 11

The consumption of fried potato as French fries (pommes frites) and potato chips (crisps) has increased significantly during the past two decades. One of the important parameters in the production of fried potatoes is level of reducing sugar. The level should remain low, because high level of reducing sugar create more Maillard reactions which contribute to unrequired levels of browning.

In order to prevent an increase in the level of reducing sugar in potatoes during storage potatoes are often sprayed with a herbicide called chlorpropham, which prevents the potato from sprouting. Sprouting induces amylases in the potato which in turn form reducing sugars.

In this study it was investigated if it is possible to improve the appearance of fried potatoes by adding HOX to sliced potatoes before frying.

Procedure

Organic grown potatoes were used in order to ensure that no herbicides has been used. The potatoes were peeled and sliced into 2 mm thick slices using a food processor. Half of the slices were immersed in a water solution of HOX containing 100 Units/ml for 3 minutes. The other half of the potato slices was immersed in water for 3 minutes. The slices were then stored in a closed container for over night (16 hours) and then fried in vegetable oil for 2 minutes at 180° C.

Results

Figure 15:
FIG. 15 shows a photograph; and,
FIG. 16 shows a diagram.
Figure 16:
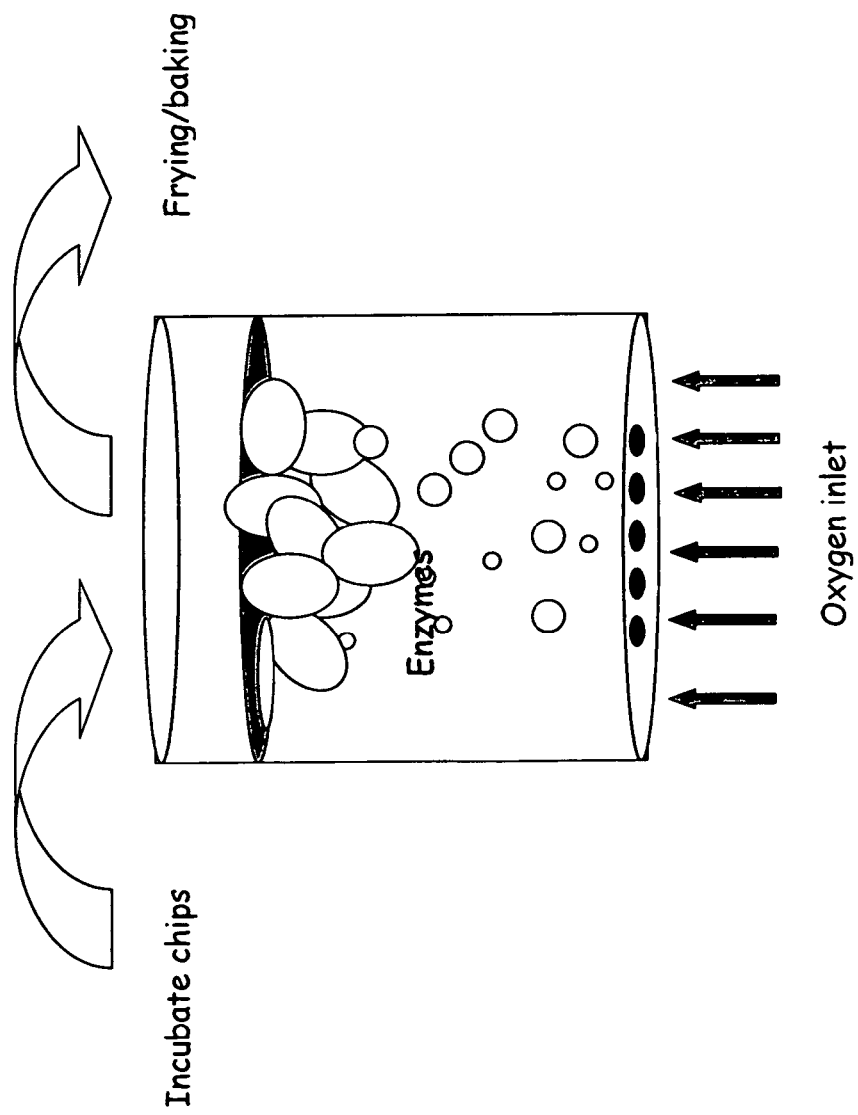

When these potato slices are fried in oil at 180° C. for 2 minutes the potato chips show some differences as shown in FIGS. 15 and 16.

Figure 14:
FIG. 14 shows a photograph.

The very brown areas of FIG. 14 is explained by a thinner potato slice in these areas and should not be taken into account for the evaluation. It is clear that potato slice treated with HOX produces a more golden surface compared with the control which is more greyish. The differences in appearance are clearer in FIG. 15 in which the golden surface of the HOX treated slice is clearly different from the control.

Conclusion

Fried potato slices prepared from potato slices treated with HOX have a lighter and more golden surface compared with control. More pronounced effects of HOX treatment are expected if the potatoes were sprouted before frying.

Example 12

Treatment of 10 kg Potato Chips by Enzyme Incubator

This example relates to treating potato chips before frying in an enzyme incubator containing an oxidoreductase utilizing any of the following sugars as substrate (glucose, maltose, sucrose and fructose) including but not limited to Hexose oxidase (EC 1.1.3.5) or Glucose oxidase (EC 1.1.3.4).

Catalase (EC 1.11.1.6) may be added in catalytic amounts with the main purpose of regeneration oxygen to a maximum level of the molar solubility in the incubation fluid (and to remove hydrogen peroxide).

Potato chips are immersed in the incubator containing a large body of water and/buffer with enzyme(s). Temperature and pH may be regulated as instrumentally possible. Beneath the incubator is an inlet for air or oxygen. The amount of enzyme and/or incubation time may be determined depending on the ratios oxygen saturation/enzyme amount/potato chip amount/incubator volume.

Materials:
- 1 HOX unit (umol $H_2O_2$/min)
- 1 Catalase unit (umol $O_2$ produced/min)
- Molar solubility of oxygen (O2) (ambient T, P and salinity): approx 250 μmol/L
- thinly sliced potatoes (100 g of potatoes contain approximately $1 \times 10-3$ moles of sugar substrate for HOX)

Incubation Procedure:

100 U of HOX and 100 U of catalase (commercial products) are added to 1 L of water at 25° C. Oxygen flow is set at a minimum of 0.015 L/min through a very fine grating. As vigorous stirring as possible which does not result in damage to the chips is implemented. Portions of 100 g are incubated for 10 minutes to a total of 100×10 min before changing the incubation solution. Alternatively sodium hydroxide or other base is added directly to the incubation solution at a rate to keep the pH at 6 (measured continuously).

The potatoes are sunsequently gently flushed with water and fried.

Using catalase combined with oxygen/air bubbling in the incubator allows for the following reduction in acrylamide. Levels of sugars are for white potato, boiled, without skin. Sugars are listed as the molar percentage left to react following treatment. Molar ratio of sugar:acrylamide is 1:1. Listed is the remaining level of acrylamid following frying as a result of treatment in the enzyme incubator.

| Treatment | fructose | glucose | sucrose | maltose | acrylamide |
|---|---|---|---|---|---|
| None | 21.07 | 30.69 | 36.3 | 12.07 | 100 |
| GOX | 21.07 | 0 | 36.3 | 12.07 | 69 |
| HOX | 21.07 | 0 | 36.3 | 6.04 | 63 |

The invention will now be further described by the following numbered paragraphs:

1. A process for the prevention and/or reduction of Maillard reaction in a foodstuff containing (i) a protein, a peptide or an amino acid and (ii) a reducing sugar, the process comprising contacting the foodstuff with an enzyme capable of oxidising a reducing group of the sugar.
2. A process according to paragraph 1 wherein the enzyme is capable of oxidising the reducing group of a monosaccharide and the reducing group of a disaccharide.
3. A process according to paragraph 1 or 2 wherein the enzyme is capable of oxidising the sugar at the 1 position.
4. A process according to paragraph 1, 2 or 3 wherein the enzyme is hexose oxidase (EC1.1.3.5).
5. A process according to any one of paragraphs 1 to 4 wherein the reducing sugar is lactose or galactose.
6. A process according to paragraph 5 wherein the reducing sugar is galactose.

7. A process according to any one of the preceding paragraphs wherein the foodstuff is a dairy foodstuff.
8. A process according to any one of the preceding paragraphs wherein the foodstuff is cheese.
9. A process according to any one of the preceding paragraphs wherein the foodstuff is mozzarella cheese.
10. A process according to any one of paragraphs 1 to 6 wherein the foodstuff is a potato or a part of a potato.
11. A process according to any one of the preceding paragraphs wherein the enzyme is contacted with the foodstuff during the production of the foodstuff.
12. A process according to any one of paragraphs 1 to 10 wherein the enzyme is contacted with the foodstuff after production of the foodstuff.
13. A process according to paragraph 12 wherein the enzyme is sprayed on the foodstuff as a solution or dispersion.
14. A process according to paragraph 13 wherein the solution/dispersion comprises the enzyme in an amount of 1-50 units Hexose Oxidase/ml.
15. A process according to any one of the preceding paragraphs wherein the process further comprises the step of contacting the foodstuff with a catalase.
16. Use of an enzyme for the prevention and/or reduction of Maillard reaction in a foodstuff containing (i) a protein, a peptide or an amino acid and (ii) a reducing sugar, wherein the enzyme is capable of oxidising a reducing group of the sugar.
17. A foodstuff prepared in accordance with the invention of any one of the preceding paragraphs.
18. A process as substantially hereinbefore described with reference to any one of Examples 1, 2, 3, 4, 5, 6, 7, 8, 9, 10 or 11.
19. A use as substantially hereinbefore described with reference to any one of Examples 1, 2, 3, 4, 5, 6, 7, 8, 9, 10 or 11.
20. A foodstuff as substantially hereinbefore described with reference to any one of Examples 1, 2, 3, 4, 5, 6, 7, 8, 9, 10 or 11.
21. An oxygen impermeable container containing a foodstuff as substantially hereinbefore described with reference to any one of Examples 1, 2, 3, 4, 5, 6, 7, 8, 9, 10 or 11.
22. A process for preventing a Maillard reaction in a foodstuff containing (i) a protein, a peptide, or an amino acid, and (ii) a reducing sugar, comprising contacting the foodstuff with hexose oxidase (EC1.1.3.5).
23. The process according to paragraph 22, wherein the reducing sugar is lactose or galactose.
24. The process according to paragraph 23, wherein the reducing sugar is galactose.
25. The process according to paragraph 23, wherein the reducing sugar is lactose.
26. The process according to paragraph 22, wherein the foodstuff is dairy foodstuff.
27. The process according to paragraph 22, wherein the foodstuff is milk based or milk containing foodstuff.
28. The process according to paragraph 22, wherein the foodstuff is cheese.
29. The process according to paragraph 22, wherein the foodstuff is mozzarella cheese.
30. The process according to paragraph 22, wherein the foodstuff contains amino acid.
31. The process according to paragraph 30, wherein the amino acid is asparagine.
32. The process according to paragraph 22, wherein the enzyme is contacted with the foodstuff during the production of the foodstuff.
33. The process according to paragraph 22, wherein the enzyme is contacted with the foodstuff after production of the foodstuff.
34. The process according to paragraph 33, wherein the enzyme is sprayed on the foodstuff as a solution or dispersion.
35. The process according to paragraph 34, wherein the solution or dispersion comprises the enzyme in an amount of 1-50 units Hexose Oxidase/ml.
36. The process according to paragraph 22, wherein the process further comprises the step of contacting the foodstuff with a catalase.
37. The process according to paragraph 22, wherein the process further comprises the step of heating the foodstuff which has been contacted with hexose oxidase to a temperature of at least 175° C.
38. The process according to paragraph 22, wherein the process further comprises the step of heating the foodstuff which has been contacted with hexose oxidase to a temperature of at least 225° C.
39. The process according to paragraph 22, wherein the process further comprises the step of heating the foodstuff which has been contacted with hexose oxidase to a temperature of greater than 260° C.
40. A foodstuff prepared in accordance with the invention in any one of paragraphs 22-39.
41. A process for preventing a Maillard reaction in a foodstuff that is heated containing (i) a protein, a peptide, or an amino acid, and (ii) a reducing sugar, comprising contacting the foodstuff with hexose oxidase (EC1.1.3.5), prior to heating.
42. The process according to paragraph 41, wherein the reducing sugar is lactose or galactose.
43. The process according to paragraph 42, wherein the reducing sugar is galactose.
44. The process according to paragraph 42, wherein the reducing sugar is lactose.
45. The process according to paragraph 41, wherein the foodstuff is dairy foodstuff.
46. The process according to paragraph 41, wherein the foodstuff is milk based or milk containing foodstuff.
47. The process according to paragraph 41, wherein the foodstuff is cheese.
48. The process according to paragraph 41, wherein the foodstuff is mozzarella cheese.
49. The process according to paragraph 41, wherein the foodstuff contains amino acid.
50. The process according to paragraph 49, wherein the amino acid is asparagine.
51. The process according to paragraph 41, wherein the enzyme is contacted with the foodstuff during the production of the foodstuff.
52. The process according to paragraph 41, wherein the enzyme is contacted with the foodstuff after production of the foodstuff.
53. The process according to paragraph 52, wherein the enzyme is sprayed on the foodstuff as a solution or dispersion.
54. The process according to paragraph 53, wherein the solution or dispersion comprises the enzyme in an amount of 1-50 units Hexose Oxidase/ml.
55. The process according to paragraph 41, wherein the process further comprises the step of contacting the foodstuff with a catalase.
56. The process according to paragraph 41, wherein the heating is to a temperature of at least 175° C.

57. The process according to paragraph 41, wherein the heating is to a temperature of at least 225° C.
58. The process according to paragraph 41, wherein the heating is to a temperature of greater than 260° C.
59. A foodstuff prepared in accordance with the invention in any one of paragraphs 41-58.
60. A process for reducing the occurrence of a Maillard reaction in a foodstuff containing (i) a protein, a peptide, or an amino acid, and (ii) a reducing sugar, comprising contacting the foodstuff with hexose oxidase (EC1.1.3.5) (HOX), wherein the reducing is in comparison with a foodstuff that has not been contacted with HOX.
61. The process according to paragraph 60, wherein the reducing sugar is lactose or galactose.
62. The process according to paragraph 61, wherein the reducing sugar is galactose.
63. The process according to paragraph 61, wherein the reducing sugar is lactose.
64. The process according to paragraph 60, wherein the foodstuff is dairy foodstuff.
65. The process according to paragraph 60, wherein the foodstuff is milk based or milk containing foodstuff.
66. The process according to paragraph 60, wherein the foodstuff is cheese.
67. The process according to paragraph 60, wherein the foodstuff is mozzarella cheese.
68. The process according to paragraph 60, wherein the foodstuff contains amino acid.
69. The process according to paragraph 68, wherein the amino acid is asparagine.
70. The process according to paragraph 60, wherein the enzyme is contacted with the foodstuff during the production of the foodstuff.
71. The process according to paragraph 60, wherein the enzyme is contacted with the foodstuff after production of the foodstuff.
72. The process according to paragraph 71, wherein the enzyme is sprayed on the foodstuff as a solution or dispersion.
73. The process according to paragraph 72, wherein the solution or dispersion comprises the enzyme in an amount of 1-50 units Hexose Oxidase/ml.
74. The process according to paragraph 60, wherein the process further comprises the step of contacting the foodstuff with a catalase.
75. The process according to paragraph 60, wherein the process further comprises the step of heating the foodstuff which has been contacted with hexose oxidase to a temperature of at least 175° C.
76. The process according to paragraph 60, wherein the process further comprises the step of heating the foodstuff which has been contacted with hexose oxidase to a temperature of at least 225° C.
77. The process according to paragraph 60, wherein the process further comprises the step of heating the foodstuff which has been contacted with hexose oxidase to a temperature of greater than 260° C.
78. A foodstuff prepared in accordance with the invention in any one of paragraphs 60-77.
79. A process for reducing the occurrence of a Maillard reaction in a foodstuff that is heated containing (i) a protein, a peptide, or an amino acid, and (ii) a reducing sugar, comprising contacting the foodstuff with hexose oxidase (EC1.1.3.5) (HOX), prior to heating, wherein the reducing is in comparison with a foodstuff that has not been contacted with HOX.
80. The process according to paragraph 79, wherein the reducing sugar is lactose or galactose.
81. The process according to paragraph 80, wherein the reducing sugar is galactose.
82. The process according to paragraph 80, wherein the reducing sugar is lactose.
83. The process according to paragraph 79, wherein the foodstuff is dairy foodstuff.
84. The process according to paragraph 79, wherein the foodstuff is milk based or milk containing foodstuff.
85. The process according to paragraph 79, wherein the foodstuff is cheese.
86. The process according to paragraph 79, wherein the foodstuff is mozzarella cheese.
87. The process according to paragraph 79, wherein the foodstuff contains amino acid.
88. The process according to paragraph 87, wherein the amino acid is asparagine.
89. The process according to paragraph 79, wherein the enzyme is contacted with the foodstuff during the production of the foodstuff.
90. The process according to paragraph 79, wherein the enzyme is contacted with the foodstuff after production of the foodstuff.
91. The process according to paragraph 90, wherein the enzyme is sprayed on the foodstuff as a solution or dispersion.
92. The process according to paragraph 91, wherein the solution or dispersion comprises the enzyme in an amount of 1-50 units Hexose Oxidase/ml.
93. The process according to paragraph 79, wherein the process further comprises the step of contacting the foodstuff with a catalase.
94. The process according to paragraph 79, wherein the heating is to a temperature of at least 175° C.
95. The process according to paragraph 79, wherein the heating is to a temperature of at least 225° C.
96. The process according to paragraph 79, wherein the heating is to a temperature of greater than 260° C.
97. A foodstuff prepared in accordance with the invention in any one of paragraphs 79-96.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:
1. A process for reducing a Maillard reaction and hence browning in cheese that is heated to at least melting comprising contacting the cheese with an enzyme prior to heating, wherein the improvement comprises the enzyme being hexose oxidase (EC1.1.3.5).
2. The process according to claim 1, wherein the cheese is mozzarella cheese.
3. The process according to claim 1, wherein the hexose oxidase (EC1.1.3.5) is contacted with the cheese during production of the cheese.

4. The process according to claim 3, wherein the hexose oxidase (EC1.1.3.5) is sprayed on the cheese as a solution or dispersion.

5. The process according to claim 1, wherein the process further comprises contacting the cheese with a catalase.

6. The process according to claim 1, wherein the heating to at least melting of the cheese comprises heating to a temperature of at least 225° C.

7. The process according to claim 1, wherein the heating to at least melting of the cheese comprises heating to a temperature greater than 260° C.

8. A cheese prepared in accordance with the process of claim 1.

9. The process according to claim 1, wherein the hexose oxidase (EC1.1.3.5) is contacted with the cheese after production of the cheese.

10. The process according to claim 9, wherein the hexose oxidase (EC1.1.3.5) is sprayed on the cheese as a solution or dispersion.

* * * * *